United States Patent [19]
Donini

[11] 3,992,514
[45] Nov. 16, 1976

[54] RADIOIMMUNOASSAY METHOD FOR HUMAN CHORIONIC GONADOTROPIN IN THE PRESENCE OF LUTEINIZING HORMONE

[75] Inventor: Pietro Donini, Rome, Italy

[73] Assignee: Istituto Farmacologico Serono S.p.A., Rome, Italy

[22] Filed: Oct. 25, 1974

[21] Appl. No.: 518,095

Related U.S. Application Data

[62] Division of Ser. No. 319,782, Dec. 29, 1972, abandoned.

[30] Foreign Application Priority Data

July 17, 1972  Italy .................................. 51583/72

[52] U.S. Cl. .............................. 424/1.5; 23/230 B; 424/12
[51] Int. Cl.² ..................... G01N 33/00; G01T 1/16; G01N 33/16
[58] Field of Search ............... 424/1.5, 12; 23/230 B

[56] References Cited
OTHER PUBLICATIONS

Jacobs, et al., Immunological Cross Reactions of LH and HCG: Contributions of the Subunits and of the Conformation of the Native Hormone, *Radioimmunoassay and Related Procedures in Medicine*, vol. I, IAEA, Vienna, 1974, pp. 237–243.

*Primary Examiner*—Benjamin R. Padgett
*Assistant Examiner*—Christine M. Nucker
*Attorney, Agent, or Firm*—Ostrolenk, Faber, Gerb & Soffen

[57] ABSTRACT

A highly specific antiserum with respect to human chorionic gonadotropin (HCG) is prepared by absorbing anti-HCG-$\beta$-subunit serum with HCG-$\alpha$-subunit. Such antiserum is suitable for use in radioimmunoassay of HCG in the presence of luteinizing hormone.

8 Claims, No Drawings

RADIOIMMUNOASSAY METHOD FOR HUMAN CHORIONIC GONADOTROPIN IN THE PRESENCE OF LUTEINIZING HORMONE

This is a division of application Ser. No. 319,782 filed on Dec. 29, 1972, now abandoned.

BACKGROUND OF THE INVENTION

Immunological hormone assay techniques rely upon the ability of a given hormone to act as an antigen in a given immunological reaction.

Based on this principle, radioimmunoassay techniques have recently been developed in which an unknown amount of unlabeled (cold) hormone to be determined is incubated — in the presence of a known amount of the same labeled hormone — with a suitable amount of a specific antiserum. Thus, an unknown amount of hormone can be easily estimated from the radioactivity count of the antigen-antibody complex through comparison with a standard curve previously constructed using known amounts of the specific antiserum, cold hormone and labeled hormone, both cold and labeled hormones having proportionally concurred (that is, in proportion to their respective amounts) in the formation of the said antigen-antibody complex. Obviously, the radioactivity count of said antigen-antibody complex is inversely proportional to the amount of cold hormone added to the reaction mixture, the antiserum and labeled hormone amounts being left unchanged.

Unfortunately, the radioimmunoassay techniques have not been applicable as yet to the determination of human chorionic gonadotropin (HCG) in the presence of comparable amounts of luteinizing hormone (LH), because of the extreme difficulty of obtaining a specific antiserum for either hormone.

On the other hand, the need of reliable means for performing such determination is particularly recognized in this field. In fact, it is known that such reliable means would permit, among other things, pregnancy to be quickly ascertained (within a few days from conception) and choriocarcinoma as well as any HCG-producing tumors to be detected and controlled.

Therefore, the enormous clinical utility of such specific antiserum in diagnosing and controlling said tumors, as well as in ascertaining pregnancy at an early stage, is clearly apparent.

Very recently Ross et al., "Structure-activity relationships of protein and polypeptide hormones," Part 1 — Reports-Proceedings of the Second International Symposium Liege, Sept. 28–Oct. 1, 1971; pages 153–7; M. Margoulies and F. C. Greenwood Editors; published by Excerpta Medica (1971) have tested antisera raised against $\alpha$ and $\beta$ subunits of HCG (hereinafter referred to as HCG-$\alpha$ and HCG-$\beta$, respectively) in radioimmunological reactions and found that the antiserum raised against HCG-$\beta$ has a higher specificity.

From a graphic display in which, among other curves, two inhibition curves of the radioimmunological reaction between anti-HCG-$\beta$ serum and labeled HCG-$\beta$ appear, which have been constructed using HCG and human pituitary LH, respectively, it can be noted that the said two inhibition curves differ in slope.

Urinary LH was not tested by Ross. Since it is known that urinary LH and pituitary LH have generally different immunological behavior, probably due to their dissimilar chemical structures and antigenic sites, no suggestion can be drawn from Ross on whether and to what extent inhibition will be produced by urinary LH on the anti-HCG-$\beta$ serum plus labeled HCG-$\beta$ system.

Furthermore, from the quantitative point of view, the two curves reported by Ross are almost coincident at least as far as the portions corresponding to low levels of cold hormone are concerned (that is, up to about 250–300 m I.U./ml).

In this respect, it should be noted that the above mentioned low hormone levels are just the levels at which a discrimination of HCG hormone from LH is required, since the physiological LH levels is urine may at most amount to 150 m I.U./ml. Consequently, the technique developed by Ross et al. cannot be used for a standard assay method of determining HCG in the presence of comparable amounts of LH.

As used herein, "m I.U." means the thousandth part of the International Unit adopted by the World Health Organization on the basis of the relevant reference preparation which is the "Second International Standard for HCG" when HCG is concerned or the "Second International Reference Preparation — HMG" when LH is concerned. Both of the said reference preparations are available from the Biological Standard Department of W.H.O., England.

As used herein "comparable amounts of LH" means amounts of this hormone (as expressed in terms of m I.U./ml) up to about 10 times those of HCG.

SUMMARY OF THE INVENTION

In accordance with the present invention, it has been found that urinary LH and HCG are immunologically discriminated in the anti-HCG-$\beta$ serum plus labeled HCG-$\beta$ system at about the same extent as pituitary LH and HCG are discriminated in the same system.

It has also been found that when an anti-HCG-$\beta$ serum is used, which has been previously absorbed with HCG-$\alpha$, the resulting inhibition curves with respect to HCG and LH are such that LH amounts at least 10 times higher than HCG amounts are required in order to achieve an equivalent degree of inhibition in the radioimmunological reaction.

The invention therefore provides a method for radioimmunologically discriminating HCG from urinary LH in which an anti-HCG-$\beta$ serum plus labeled HCG-$\beta$ system is used.

The invention also provides a novel highly specific antiserum for radioimmunoassay which is obtained by absorbing anti-HCG-$\beta$ serum with HCG-$\alpha$ subunit.

The invention further provides a method for the radioimmunoassay of HCG in presence of comparable amounts of LH in which an HCG-$\alpha$-absorbed anti-HCG-$\beta$ serum plus labeled HCG-$\beta$ system is used to discriminate HCG from LH. Such method is particularly suitable for use in ascertaining pregnancy at an early stage.

DETAILED DESCRIPTION OF THE INVENTION

The anti-HCG-$\beta$ serum from which the highly specific antiserum of this invention is obtained can be prepared, as usual, by injecting human HCG-$\beta$ in such heterologous anumals as rabbit, sheep, goat, guinea-pig and so on.

For the sake of convenience a common laboratory animal is preferred, particularly the rabbit.

An immunization schedule has been used which is similar to that suggested by Ross. It is understood, however, that the invention is not restricted to this particular immunization schedule, since the later may be changed according to the kind of animal, the special adjuvants used and so on.

In general, the absorption of anti-HCG-β serum is performed using such HCG-α amounts that the highest specificity is ultimately achieved in the antiserum. Such amounts can somewhat vary according to the particular antiserum used. According to the present invention, they usually range from 0.05 to 2 mg. HCG-α per ml. anti-HCG-β serum; a preferred range is from 0.1 to 0.4 mg HCG-α per ml. anti-HCG-β serum.

As used herein, the term "absorption" has its generally accepted meaning in immunology, that is, it refers to a procedure of reacting an antiserum with a given antigen in order to remove from the antiserum the antibody specifically reacting with that antigen. Time and temperature conditions of such immunological reaction are not critical. The reaction leads to an insoluble antigen-antibody complex which is centrifuged and discarded to give an "absorbed" (purified) antiserum supernatant.

The following Example 1 illustrates a typical preparation of the anti-HCG-β serum whereas Example 2 illustrates the absorption of the above antiserum to give the highly specific antiserum of this invention.

EXAMPLE 1

Preparation of anti-HCG-β serum

Using intradermic injections administered at multiple body sites, each of a group of rabbits was given an ultra-sound homogenized mixture consisting of 50 γ (micrograms) HCG-β dissolved in 1 ml. physiological salt solution plus 1 ml. Freund's complete adjuvant (Difco) plugs 5 mg. dried tubercle mycobacteria (H37RA Difco).

In a separate body site, each rabbit was subcutaneously given 0.5 ml. pertussis vaccine.

One month later, a mixture was injected intradermally which consisted of 50 γ HCG-β dissolved in 1 ml. physiological salt solution plus 1 ml. Freund's complete adjuvant.

The animals were first bled by puncture of the marginal ear vein one week after the last mentioned injection. The blood, collected in an Erlenmeyer flask, was allowed to clot by maintaining the flask inclined at room temperature for about 4 hours, and then left standing overnight at 4° C. The coagulated blood was centrifuged the next morning to separate serum to which sodium azide (1 to 10,000 weight/volume) was added. In this context, parts by weight and parts by volume bear the same relation as do milligrams and milliliters.

The animals were bled weekly thereafter. When the antiserum titer tended to decrease, the animals were subcutaneously given a booster injection consisting of 50 γ HCG-β dissolved in 1 ml. physiological salt solution.

EXAMPLE 2

Absorption of anti-HCG-β serum with HCG-α

0.2 mg. HCG-α was added to 1 ml. anti-HCG-β serum. The mixture was kept for 2 hours at 37° C in a thermostat and then for 24 hours at 4° C. A precipitate formed which was centrifuged and discarded.

The absorbed antiserum supernatant was found to be highly specific with respect to HCG in the presence of comparable amounts of LH.

The following Example 3 shows that the anti-HCG-β serum plus labeled HCG-β system is able to discriminate between HCG and urinary LH at about the same extent as HCG and pituitary LH are discriminated in the same system.

EXAMPLE 3

An anti-HCG-β serum which had been prepared in accordance with Example 1 was suitably diluted with a 0.01M phosphate buffer at pH 7.5 containing normal rabbit serum (1:1000), tetrasodium ethylenediaminetetraacetate (0.014M) and bovine serum albumin (0.25%).

Using the same buffer which, however, did not contain the rabbit serum, three series of solutions having gradually varied concentrations were prepared containing a commercial HCG preparation (Roussel, 3200 I.U./mg.), a urinary LH preparation (100 I.U./mg.) and a pituitary LH preparation (1300 I.U./mg.), respectively.

A HCG-β preparation, which had been labeled with $^{125}I$ in accordance with the Chloramine-T method described in Greenwood et al., Biochem. J. 89, 114 (1963), was suitably diluted with the same buffer used to prepare the above mentioned HCG and urinary or pituitary LH solutions.

A fixed amount of diluted anti-HCG-β serum was incubated for 24 hours at 37° C with an aliquot part of each of the HCG or LH solutions. To each of the incubation mixtures, an amount corresponding to 10,000 counts per minute of labeled HCG-β was added. Incubation was continued at 37° C for 24 hours, and anti-rabbit-gammaglobulin serum was added in a sufficient amount to precipitate the formed antigen-antibody complex. After further incubation at 37° C for 24 hours, the precipitate was separated from the supernatant by centrifugation, the latter being discarded. Finally, the precipitate radioactivity was counted.

An inhibition curve was constructed for each of the three hormones; in said curves the precipitate radioactivity was plotted against the hormone concentration. From the comparison between the three curves so obtained, it could be observed that 27 m I.U./ml. HCG, 109 m I.U./ml. urinary LH and 110 m I.U./ml. pituitary LH, respectively, were needed to achieve 50% inhibition of the reaction between anti-HCG-β serum and labeled HCG-β.

The following Examples 4 and 5 show that urinary or pituitary LH amounts more than 10 times higher than HCG amounts are necessary in order to achieve an equivalent degree of inhibition of the radioimmunological reaction when an HCG-α-absorbed anti-HCG-β serum plus labeled HCG-β system is used to discriminate HCG from LH.

EXAMPLE 4

An anti-HCG-β serum which had been absorbed with HCG-α in accordance with Example 2 was diluted 1 to 2000 with a 0.01 M phosphate buffer at pH 7.5 containing normal rabbit serum (1:1000), tetrasodium ethylenediaminetetraacetate (0.014M) and bovine serum albumin (0.25%).

Using the same buffer which, however, did not contain the rabbit serum, two series of solutions having gradually varied concentrations were prepared containing a commercial HCG preparation (Roussel, 3200 I.U./mg.) and a urinary LH preparation (100 I.U./mg.), respectively.

A HCG-β preparation, which had been labeled with $^{125}$I in accordance with the Chloramine-T method described in Greenwood et al., Biochem. J. 89, 114 (1963), was suitably diluted with the same buffer used to prepare the above mentioned HCG and LH solutions.

A fixed amount of diluted anti-HCG-β serum was incubated for 24 hours at 37° C with an aliquot part of each of the HCG or LH solutions. To each of the incubation mixtures, an amount corresponding to 10,000 counts per minute of labeled HCG-β was added. Incubation was continued at 37° C for 24 hours, and anti-rabbit-gammaglobulin serum was added in a sufficient amount to precipitate the formed antigen-antibody complex. After further incubation at 37° C for 24 hours the precipitate was separated from the supernatant by centrifugation, the latter being discarded. Finally, the precipitate radioactivity was counted.

An inhibition curve was constructed for each of the two hormones; in said curves the precipitate radioactivity was plotted against the hormone concentration. From the comparison between the two curves so obtained, it could be observed that 45 m I.U./ml. HCG and 523 m I.U./ml. LH, respectively, were needed to achieve 50% inhibition of the reaction between anti-HCG-β serum and labeled HCG-β.

EXAMPLE 5

The procedure described in Example 4 was repeated to effect similar radioimmunoassays, except that the urinary LH preparation was replaced with a pituitary LH preparation (1300 I.U./mg).

The comparison between the two curves constructed as described above showed that 44.8 m I.U./ml. HCG and 559 m I.U./ml. LH, respectively, were needed to achieve 50% inhibition of the reaction between anti-HCG-β serum and labeled HCG-β.

As illustrated by the Examples hereinafter, the assay method based on the use of the highly specific antiserum of this invention can be applied to the radioimmunoassay of HCG in the presence of LH not only in a buffered, e.g., phosphate buffered, solution of the hormones but even directly in a sample of human urine.

As stated above, the physiological LH levels in urine may at most amount to 150 m I.U./ml. Therefore, the novel highly specific antiserum of this invention is able to detect HCG amounts as low as about 15 m I.U./ml. in the presence of physiological amounts of LH.

EXAMPLE 6

The procedure described in Example 4 was repeated to effect similar radioimmunoassays, except that the HCG or LH solutions in the incubation mixtures were replaced with urine samples collected from normally menstruating women during the luteal phase.

In no case, a significant (that is, higher than about 20%) degree of inhibition of the radioimmunological reaction between anti-HCG-β serum and labeled HCG-β was observed.

EXAMPLE 7

The procedure described in Example 4 was repeated to effect similar radioimmunoassays, except that the HCG or LH solutions in the incubation mixtures were replaced with urine samples collected from early pregnant women (6 to 12 days after ovulation and coitus). The tested samples gave degrees of inhibition ranging from 20 to 70%.

EXAMPLE 8

To a urine sample collected during the luteal phase of menstrual cycle (physiological LH level of 10 to 15 m I.U./ml.), gradually varied amounts of commercial HCG were added.

From radioimmunoassays performed in accordance with the procedure described in Example 4, a significant degree of inhibition was observed for HCG amounts higher than 20–25 m I.U./ml.

To a similar urine sample, gradually varied amounts of LH were added. A significant degree of inhibition could not be observed until LH amounts of at least 200 m I.U./ml. were added.

Various changes and modifications can be made in the process and products of this invention without departing from the spirit and the scope thereof. The various embodiments set forth herein were intended to further illustrate the invention but were not intended to limit it.

What we claim is:

1. A method for radioimmunologically discriminating human chorionic gonadotropin from urinary luteinizing hormone in a specimen which comprises mixing the specimen with anti-human chorionic gonadotropin - β serum and radioactively labeled human chorionic gonadotropin - β, and thereafter determining the degree of inhibition of the immunological reaction between the anti-human chorionic gonadotropin-β and the labeled human chorionic gonadotropin-β.

2. The method of claim 1 wherein the inhibition is determined by effecting a radioimmunological assay of the mixture and comparing the results with a known standard.

3. A radioimmunological method for quantitatively determining human chorionic gonadotropin in a specimen containing human chorionic gonadotropin in the presence of up to about 10 times the amount in m I.U./ml of luteinizing hormone, which comprises mixing the specimen to be tested with human chorionic gonadotropin-α-absorbed anti-human chorionic gonadotropin-β serum and radioactively labeled human chorionic gonadotropin-β, and thereafter determining the degree of inhibition of the immunological reaction between the human chorionic gonadotropin-α-absorbed anti-human chorionic gonadotropin β serum and the labeled human chorionic gonadotropin β, the observed inhibition being substantially due to human chorionic gonadotropin.

4. The method of claim 3 wherein the inhibition is determined by effecting a radioimmunological assay of the specimen and comparing the results with a known standard.

5. The method of claim 3 wherein each milliliter of anti-human chorionic gonadotropin-β serum was absorbed with about 0.05–2 milligrams of human chorionic gonadotropin-α.

6. The method of claim 3 wherein each milliliter of anti-human chorionic gonadotropin-β serum was absorbed with 0.1 to 0.4 milligrams of human chorionic gonadotropin-α.

7. A method for radioimmunologically ascertaining pregnancy which comprises effecting the method of claim 6 using a sample of urine as the specimen, pregnancy being positively ascertained when the inhibition is greater than about twenty percent.

8. A method for radioimmunologically ascertaining pregnancy which comprises effecting the method of claim 3 using a sample of urine as the specimen, pregnancy being positively ascertained when the inhibition is greater than about 20 percent.

* * * * *